US009927634B2

(12) United States Patent
Portney

(10) Patent No.: US 9,927,634 B2
(45) Date of Patent: Mar. 27, 2018

(54) SWITCHABLE SPECTACLES

(71) Applicant: Valdemar Portney, Newport Coast, CA (US)

(72) Inventor: Valdemar Portney, Newport Coast, CA (US)

( * ) Notice: Subject to any disclaimer, the term of this patent is extended or adjusted under 35 U.S.C. 154(b) by 11 days.

(21) Appl. No.: 15/155,401

(22) Filed: May 16, 2016

(65) Prior Publication Data

US 2016/0259181 A1    Sep. 8, 2016

Related U.S. Application Data

(62) Division of application No. 13/626,118, filed on Sep. 25, 2012, now Pat. No. 9,364,319.

(51) Int. Cl.
*G02C 7/08* (2006.01)
*G02C 7/06* (2006.01)
(Continued)

(52) U.S. Cl.
CPC ............ *G02C 7/085* (2013.01); *A61F 2/1627* (2013.01); *A61F 2/1654* (2013.01); *G02B 3/12* (2013.01);
(Continued)

(58) Field of Classification Search
CPC . G02C 7/06; G02C 7/061; G02C 7/08; G02C 7/081; G02C 7/083; G02C 7/085;
(Continued)

(56) References Cited

U.S. PATENT DOCUMENTS 4,418,990 A * 12/1983 Gerber .................. G02C 7/085
351/158

4,435,856 A    3/1984 L'Esperance
(Continued)

FOREIGN PATENT DOCUMENTS

EP         0 212 616 A2    3/1987
WO    2001 097742 A2    12/2001
(Continued)

OTHER PUBLICATIONS

Guoqiang Li, et al.; "Switchable electro-optic diffractive lens with high efficiency for ophthalmic applications"; Proceedings of the National Academy of Science of the USA, 2006; Apr. 18, 2006; pp. 6100-6104; vol. 103.
(Continued)

*Primary Examiner* — William R Alexander
(74) *Attorney, Agent, or Firm* — Hackler Daghighian Martino & Novak

(57) ABSTRACT

A pair of spectacles has a frame and defines a horizontal plane generally through the temples and bridge of the spectacles. At least one switchable lens is configured to switch its foci from a first focal length to a second focal length. An infrared emitter is disposed at one peripheral edge of the at least one switchable lens, the infrared emitter configured to emit an infrared radiation. An infrared sensor is disposed at an opposite peripheral edge, the infrared sensor configured to detect a different intensity of the infrared radiation from the infrared emitter upon reflection from the front surface of wearer's eye ball. The at least one switchable lens is configured to switch to its first focal length when the infrared sensor detects the infrared radiation and is configured to switch to its second focal length when the infrared sensor detects a different intensity of the infrared radiation.

14 Claims, 6 Drawing Sheets

(51) Int. Cl.

| | |
|---|---|
| *G02B 27/42* | (2006.01) |
| *G02C 7/02* | (2006.01) |
| *G02B 3/12* | (2006.01) |
| *A61F 2/16* | (2006.01) |
| *G02C 11/00* | (2006.01) |
| *A61F 2/14* | (2006.01) |

(52) U.S. Cl.
CPC ............... *G02B 27/42* (2013.01); *G02C 7/02* (2013.01); *G02C 7/06* (2013.01); *G02C 7/081* (2013.01); *G02C 7/083* (2013.01); *G02C 11/10* (2013.01); *A61F 2/14* (2013.01); *G02C 7/08* (2013.01); *G02C 2202/20* (2013.01)

(58) Field of Classification Search
CPC . G02C 7/02; G02C 11/10; G02B 3/12; G02B 27/42; A61F 2/1627; A61F 2/1654; A61F 2/14
USPC .......................... 359/571; 351/159.39, 159.4
See application file for complete search history.

(56) References Cited

U.S. PATENT DOCUMENTS

| | | | | |
|---|---|---|---|---|
| 4,702,575 | A * | 10/1987 | Breglia | ................. A61B 3/113 351/210 |
| 4,890,903 | A | 1/1990 | Treisman et al. | |
| 4,932,966 | A | 6/1990 | Christie et al. | |
| 5,956,183 | A | 9/1999 | Epstein et al. | |
| 6,445,509 | B1 | 9/2002 | Marvin | |
| 7,538,744 | B1 * | 5/2009 | Liu | ........................ G06F 3/013 345/7 |
| 2002/0140899 | A1 * | 10/2002 | Blum | ................... G02B 27/017 351/159.03 |
| 2005/0030474 | A1 * | 2/2005 | Sumiya | ..................... G01J 9/00 351/211 |
| 2005/0143814 | A1 | 6/2005 | Esch et al. | |
| 2005/0288785 | A1 | 12/2005 | Portney et al. | |
| 2007/0010880 | A1 | 1/2007 | Esch | |
| 2007/0030573 | A1 | 2/2007 | Batchko et al. | |
| 2007/0032866 | A1 | 2/2007 | Portney | |
| 2009/0033866 | A1 | 2/2009 | Blum et al. | |
| 2009/0256977 | A1 | 10/2009 | Haddock et al. | |
| 2009/0310221 | A1 | 12/2009 | Aschwanden | |
| 2010/0066973 | A1 | 3/2010 | Portney | |
| 2012/0140167 | A1 | 6/2012 | Blum | |
| 2013/0141690 | A1 * | 6/2013 | Taylor | ..................... G02C 7/08 351/159.39 |
| 2013/0278889 | A1 * | 10/2013 | Lapstun | ................. G02C 7/083 351/159.4 |

FOREIGN PATENT DOCUMENTS

| | | | |
|---|---|---|---|
| WO | 2004 046768 | A2 | 6/2004 |
| WO | 2008 091859 | A1 | 7/2008 |
| WO | 2009 126946 | A1 | 10/2009 |

OTHER PUBLICATIONS

Dean Faklis, et al.; "Spectral properties of multiorder diffractive lenses"; Applied Optics; May 10, 1995; pp. 2462-2468; vol. 34, No. 14; Optical Society of America.

Valdemar Portney; "Light distribution in diffractive multifocal optics and its optimization"; J Cataract Refract Surg 2011; 37: 2053-2059; Elsevier Inc.

* cited by examiner

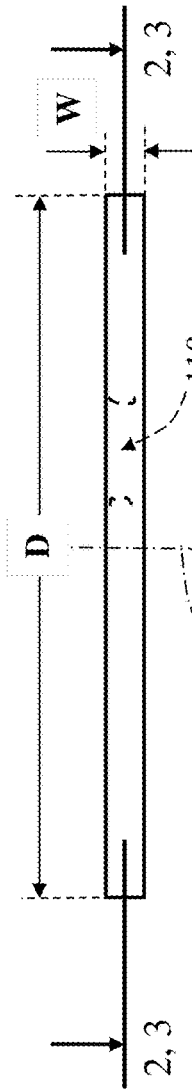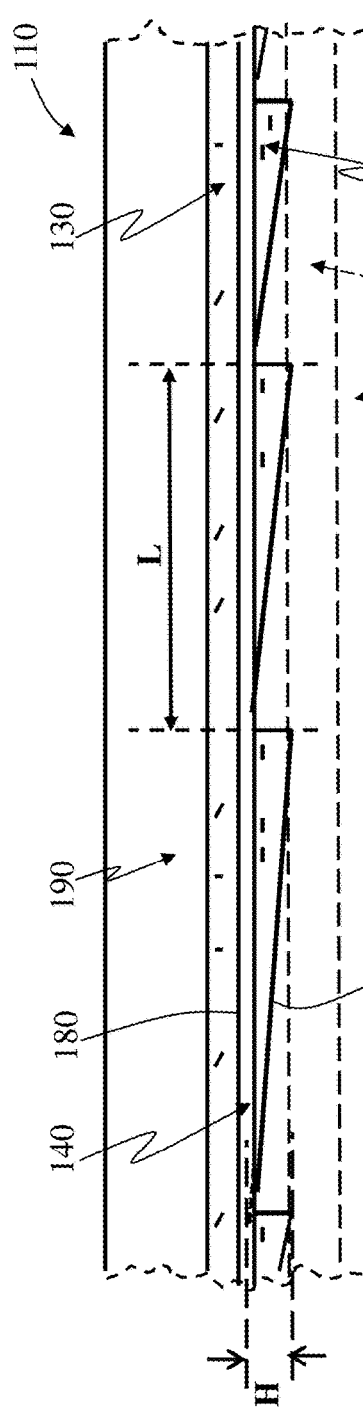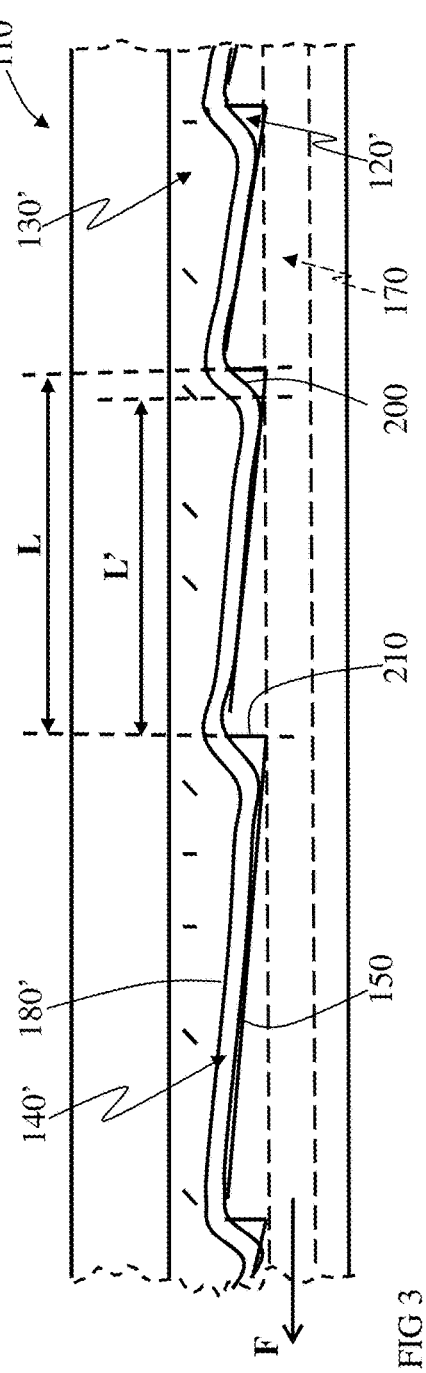

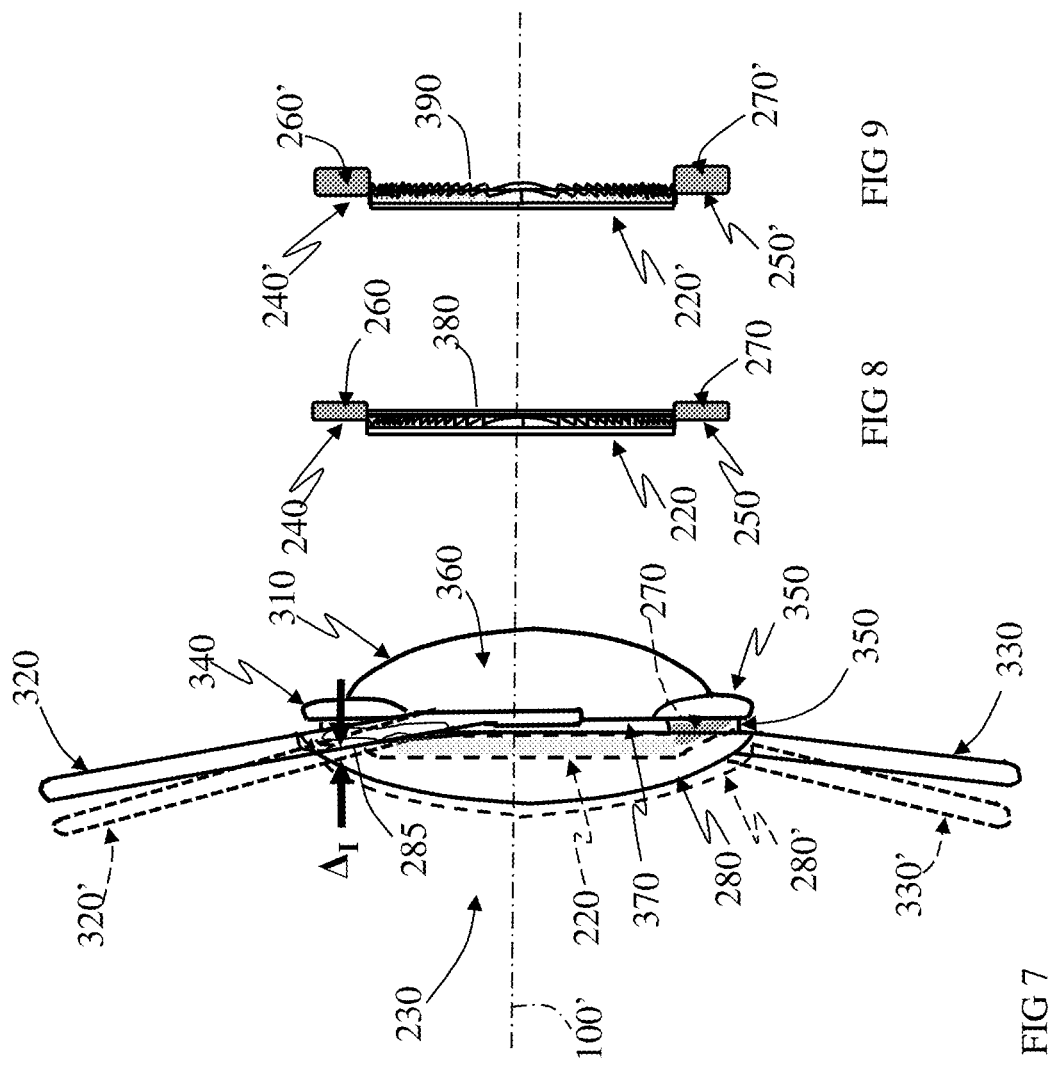

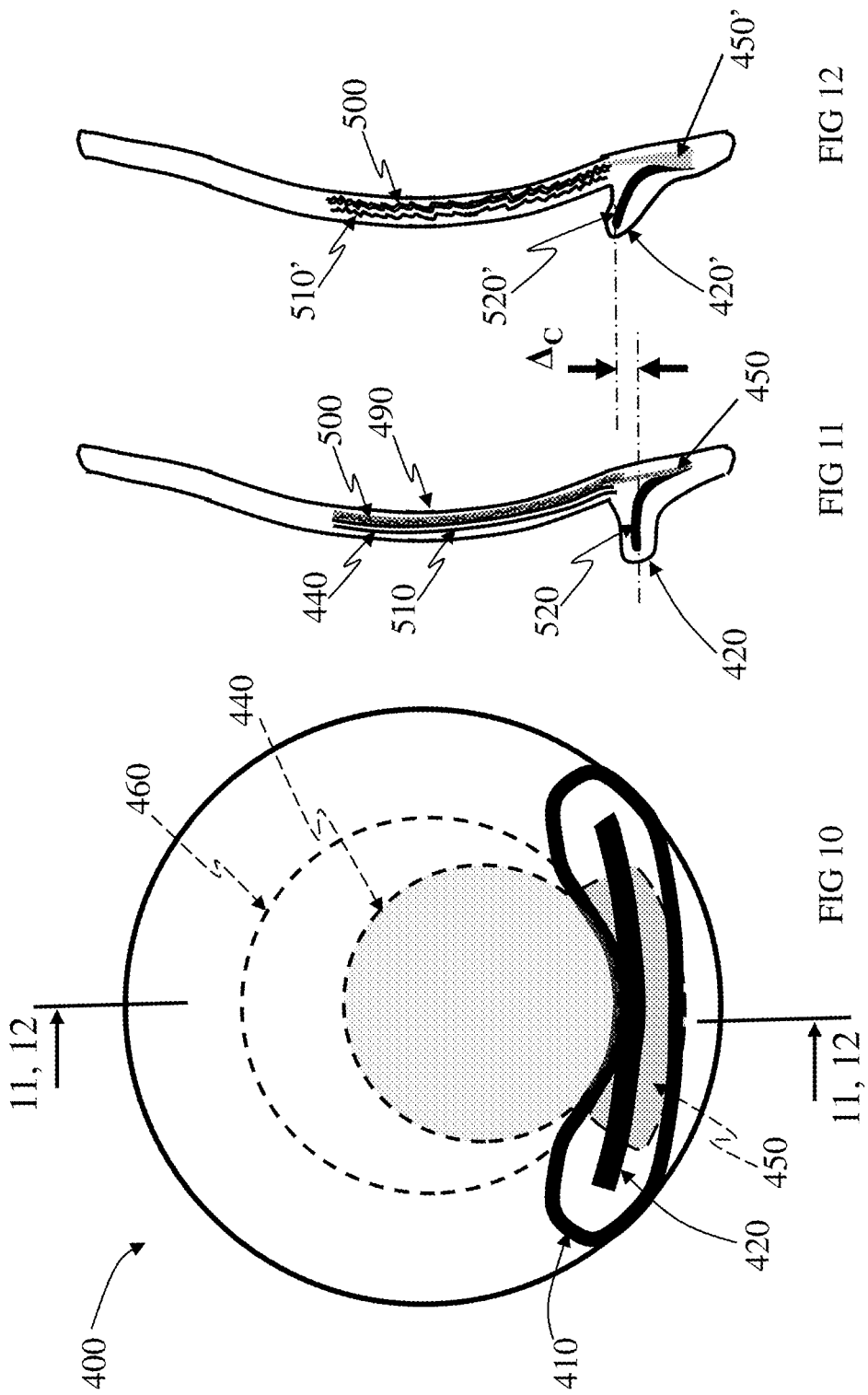

SWITCHABLE SPECTACLES

CROSS-REFERENCE TO RELATED APPLICATIONS

This divisional application claims priority to application Ser. No. 13/626,118 filed on Sep. 25, 2012, the entire contents of which are fully incorporated herein with this reference.

FIELD OF THE INVENTION

The present invention generally relates to a switchable lens configured to switch its foci from a first focal length to a second focal length. More specifically, an infrared emitter is disposed at one peripheral edge of a lens and/or frame and an infrared sensor is disposed at an opposite peripheral edge, where the infrared sensor is configured to detect a different intensity of the infrared radiation from the infrared emitter upon reflection from the front surface of wearer's eye ball. The at least one switchable lens is configured to switch to its first focal length when the infrared sensor detects the infrared radiation and is configured to switch to its second focal length when the infrared sensor detects a different intensity of the infrared radiation.

BACKGROUND OF THE INVENTION

The refractive-diffractive switchable lens or diffractive switchable lens of the present invention can be applied outside or within ophthalmic application. In latter case the lens can be called diffractive switchable ophthalmic lens. Ophthalmic lens in the present invention is defined as a diffractive switchable lens suitable for placement outside the eye such as spectacle lens or contact lenses or inside the eye such as aphakic and phakic intraocular lenses or implants placed in posterior or anterior eye chamber and also included are artificial corneas and corneal implants or inlay. For detailed explanation of the lens of the present invention, the ophthalmic application for presbyopia correction is used as a preferred embodiment.

A fixed single power lens provides good quality vision but only within a small range of viewing distances that is usually significantly narrower than the range required from near to far vision. The resulted vision deficiency is called Presbyopia. There is a significant effort to develop a lens for Presbyopia correction in a form of multifocal refractive or diffractive type lenses that provide multiple foci and also in a form of accommodating lenses that may change their optical surface shapes or positions inside the eye for ocular power increase for near vision. Diffractive switchable optical element according to the present invention is a lens that consequently changes the image positions between distance and near foci or fields by directing light to refractive focus and a different focus position corresponding to a diffraction order. Usually but not necessary the power corresponding to diffraction order is higher the refractive power and this difference is called Add power as a traditional reference to a power difference between near and far foci in presbyopia correction. A refractive-diffractive switchable ophthalmic lens implanted inside the eye is also called diffractive accommodating lens as switching between far and near foci occurs under the action of ciliary muscle. It is important to note that diffractive switchable lens according to the present invention has application outside ophthalmic one in so called engineering optic (microscopes, telescopes, photo-objectives, etc.).

Portney's U.S. application Ser. No. 13/247,840, "Switchable Diffractive Accommodating Lens" explained accommodation, ciliary muscle action during accommodation and prior art involving in Presbyopia correction. The same Application also disclosed Sensor Cell that functioned for (a) sensing a need to focus for far or near and/or (b) actuation of an implantable accommodating lens (phakic, aphakic, corneal inlay) to focus at far or near by a direct interaction with ciliary muscle at the location of the ciliary spur. Equivalent Sensor Cell can also be used with a diffractive accommodating lens of the present invention.

The advantage of the diffractive switchable optic in switching between far and near foci over a refractive optic was described in Portney' U.S. application Ser. No. 13/247,840, "Switchable Diffractive Accommodating Lens" and also by a large group of researches: Li G, Mathine D L, Valley P, et al. "Switchable electro-optic diffractive lens with high efficiency for ophthalmic application", Proceedings of the National Academy of Science of the USA, 2006; 103: 6100-6104, in the application to the spectacle lens. The operation of the described by Li G, et al spectacle lens was based on electrical control of the refractive index of thin layer of pneumatic liquid crystal by creating volume diffractive element through refractive index modulation. Though the approach is feasible, it is complicated and expensive to execute and it also requires electric field for its operation which is a challenge for ocular implant or contact lens application. Haddock et al. in US Patent Application 20090256977 introduced further improvement to the above volume diffractive lens manufacturability. The spectacle lenses according to the above design were released by PixelOptics under EmPower name. Similar technology is under development for accommodating IOL by ELENZA, Inc.

A diffractive switchable lens according to the present invention incorporates a switchable cell and optical surfaces. A switchable cell of the present invention is an opto-mechanical device that utilizes mechanical optical switching between far and near foci by changing the optical surface shape between refractive continuous form for one focal position and diffractive form of a periodic structure for a different focal position. Refractive surface focusing ability depends on surface curvatures and diffraction surface focusing ability depends on a diffraction surface periodic structure. An optical surface can be part of a switchable cell or part of a separate optical element that together form diffractive switchable lens. Switchable cell is the center of the present invention for operation of a diffractive switchable lens.

Diffractive optic has been described by a huge volume of papers. For instance, D Faklis and D M Morris, "Spectral properties of multiorder diffractive lenses", Apply Optics 1995; 34(14): 2462-2468, described diffractive optic of blazed shape, so called surface relief shape of different diffraction orders. This type of diffractive optic is called Kinoform that allows 100% of light to be directed to a single focal position formed by a single diffraction order or multiorder per Faklis and Morris explanation. Diffraction zones forming diffraction surface periodic structure can be of different profiles, rectangular, sine-wave for instance, as well as blazed surface of different profiles (parabolic, linear, sine) of a single order or multiorder composition and any one or a combination of them can be applied to a diffractive switchable lens of the present invention for so called diffraction guiding surface introduced below.

The advantage in using diffractive element is that the focal length of selected diffraction order is defined only by the periodic structure of the diffraction surface which can be built into the diffraction surface design. By the law of formation of a diffraction order, light can only be channeled along discrete diffraction orders of the diffractive lens where light constructive interference can take place thus providing predetermined separation between refractive and diffractive foci or Add power in ophthalmic application. Thus, a difference between refractive and diffractive focal positions of the diffractive accommodating lens of the present invention is predetermined by the switchable cell design itself and not by an external factor as in all refractive accommodating lens designs which makes them inherently unpredictable.

An image is physically formed at a given focus of a diffraction order if a significant percent of total light is actually channeled alone the given diffraction order. This depends on the light phase shift introduced by each diffraction zone, i.e. diffraction groove height or periodic surface modulation amplitude. There are a lame number of papers explanting a diffractive lens light distribution and V. Portney, "Light distribution in diffractive multifocal optics and its optimization", J Cataract Refract Surg 2011; 37:2053-2059, offers an explanation in terms of multifocal optics and for blazed diffraction surfaces.

In a simple paraxial form the circular diffraction zones, also called grooves, echelettes or surface-relief profile, can be expressed by the formula:

$$r_j = \sqrt{2 \cdot j \cdot m \cdot \lambda_{design} \cdot F_m} \quad (1)$$

where grooves radii ($r_j$) create spherical wavefront of focal length ($F_m$) for a given diffraction order (m) and design wavelength ($\lambda_{design}$).

In case of surface relief profile and in paraxial approximation, the blaze material thickness ($H_m$) to produce 100% efficiency at the focus of m-order diffraction is $$H_m = \frac{m \cdot \lambda_{design}}{(n - n')} \quad (2)$$

where n=refractive index of the lens material and n'=refractive index of the medium adjacent to the diffraction surface.

In case of small spherical aberration, the periodic structure, i.e. diffraction groove periods of the diffractive optic is quite accurately defined by the Eq. 1 for a given focal distance. In case of a significant spherical aberration of a diffractive lens introduced to extend a range of foci around a focus of a selected diffraction order, the calculation of the groove shapes can be conducted numerically equivalent to the method described by Portney in the US Patent Appl. No: 20100066973 for multifocal diffractive lens.

Portney' U.S. application Ser. No. 13/247,840, "Switchable Diffractive Accommodating Lens" disclosed diffractive optic with specific adjustment of its periods to create positive spherical aberration which is the most effective for depth of focus increase at a diffraction order. The same form of the diffraction surface periodicity can also be applied to the guiding surface of the diffractive switchable lens of the present invention to expand a range of foci at its diffractive focus.

SUMMARY OF THE INVENTION

A switchable cell in accordance with the present invention consists of at least three elements: (1) optical substrate with diffraction surface on it, (2) elastic film in close proximity or contact with the diffraction surface of the optical substrate, and (3) chamber between elastic film and diffraction surface of the optical substrate filled with optical fluid of refractive index which is equal to or up to about 0.03 unit different from the refractive index of the optical substrate. The chamber is called "transparent chamber" and the optical fluid is called "matching fluid" because desirably, its refractive index matches the refractive index of the optical substrate at least at one of wavelengths. The matching is important in the visual spectrum and desirable in green color part of the spectrum in ophthalmic application. This three elements combination forms "3-element switchable cell". Film that is in contact with the optical substrate diffraction surface is preferable option because it provides more stable switchable cell structure and minimizes the amount of matching fluid transfer for the switchable cell operation. A proximate film position is also possible, say less than about 1 mm between the film and diffraction surface of the optical substrate.

A switchable cell may also consists of five elements: (1) elastic film, (2) optical substrate with diffraction surface, (3) transparent chamber between the elastic film and optical substrate diffraction surface filled with matching fluid, (4) optical membrane situated next to the elastic film at the opposite side from the optical substrate and (5) chamber between the elastic film and optical membrane filled with optical fluid of the refractive index that is differ from the refractive index of the optical substrate at the wavelengths of the switchable cell operation, this is so called "non-matching fluid". The corresponding chamber is called "active chamber". A switchable cell consisting of five elements listed above is called "5-element switchable cell". Thus, 5-element switchable cell comprises of 3-element switchable cell plus optical membrane forming active chamber with elastic film filled with non-matching fluid. The medium exterior to the film at the opposite side from the transparent chamber can be aqueous humor, air, stroma, tear layer, etc., depending on the application of the diffractive switchable lens of the present invention. The exterior medium is either ambient medium in case of 3-element switchable cell or a medium of the active chamber in case of 5-element switchable cell.

The optical substrate or optical membrane each may include flat or curved optical surface either at front or back surface or both surfaces. In a general form, diffractive switchable lens of the present invention consists of front and back optical surfaces and switchable cell situated between them. The diffraction surface of the optical substrate that faces the elastic film is called "guiding surface". Surface relief or blazed shape of the guiding surface is preferable embodiment because it provides highest diffractive efficiency, i.e. largest percent of light concentration in a single diffractive focus. The corresponding surface type will be used in explaining a diffraction switchable optical element of the present invention.

The operation of a switchable cell relies on the ability of matching fluid to optically mask the guiding surface resulting in optical interaction with light by the matching fluid surface shaped by the film instead of an interaction with the guiding surface. Depending how the film shapes the matching fluid, different optical characteristics can be created: (a) refractive surface shape to create refractive state with its refractive focus or, (b) diffraction surface shape with periodic structure to create diffractive state with its diffractive focus. The film itself does not contribute to a focusing ability of switchable cell because of being largely of uniform thickness and, as result, its front and back surfaces are parallel to each other, i.e. they manifest equivalent curvatures/power profiles within the thickness contribution. The external surface of the film facing the external medium is called "formable surface". Because a shape of the matching fluid formed by the film and the formable surface shape are equivalent, the formable surface is used in describing refractive or diffractive state of a switchable cell instead of referencing to a matching fluid surface shaped by the film. Thus, a focusing ability of a switchable cell is defined by the formable surface shape and a difference in refractive indices between non-matching fluid and the optical substrate (substrate).

Refractive formable surface is formed if no pressure difference exists between active and transparent chambers. This is so called relaxed state of a switchable cell as no external actuation is required in the relaxed state. In this condition the formable surface takes largely a shape of a minimum strain or, more specifically, the based surface of the diffraction guiding surface if the film is in contact with the guiding surface. Diffractive formable surface is formed if a pressure in transparent chamber is below a pressure in active chamber or medium exterior to the film and the film largely takes the shape of the guiding surface due to its elasticity. It takes place at some pressure difference called threshold level. This is so called active state of the switchable cell as a pressure difference requires an external actuation. In case of a diffraction guiding surface being a surface relief, i.e. a Kinoform, the formable surface also takes the same Kinoform surface shape to focus light at the focus position defined by the diffraction guiding surface. This is the reason to apply term "guiding" to the diffraction surface of the optical substrate as it "guides" the film shape in the active state.

The film itself is either free-standing or bonded to the guiding surface at the ridges of the diffractive grooves and its shape and, therefore, the shape of the formable surface is defined by the base surface of the diffractive guiding surface in the relaxed state. Formable refractive surface in relaxed state can be flat, curved and aspherized, i.e. of any possible shape of a base surface of the diffraction guiding surface.

There is advantage to allocate relaxed state of a switchable cell in ophthalmic application to provide far focus because of a safety consideration as far focus is desirable fall back state if an actuation of the active state fails. Therefore, the active state is to provide diffractive focus for near focus. In addition, an image formed at the diffractive focus is commonly acceptable for near vision as demonstrated by extensive clinical experience with diffractive multifocal IOLs. In general, it can be in reverse, i.e. far focus or longer focal length is formed by the diffractive focus in active state and near focus or shorter focal length by the refractive focus in relaxed state. In general, switchable states may include at least two active states in addition to refractive state or instead of refractive state with each of these active states providing its own focus position and the switching takes place between two diffractive foci.

The central advantage of a switchable cell according to the present invention is that the refractive focus of the relaxed state coincides with zero order diffractive focus formed by the formable surface Kinoform in the active state producing an image at a non-zero diffractive focus. A separation between the corresponding non-zero diffractive focus and zero order diffractive focus is only controlled by the built-in periodicity of the guiding surface which is responsible for the periodicity of the formable surface in the active state. Therefore, a separation between refractive focus in the relaxed state and diffractive focus in the active state is also controlled only the periodicity of the guiding surface.

The present invention references to a "near focus" provided by an active state of a switchable cell in an ophthalmic application but it can be an intermediate focus or even multi-foci combination if guiding surface is of a multi-zonal structure with each zone providing its own diffractive focus. In general, a reference to a "near focus" used in the present invention is a focus that differs from far focus, i.e. "near focus" may technically reference to near or intermediate focus in terms its correspondence to near or intermediate vision.

A pressure difference between active and transparent chambers of a switchable cell of the present invention is created either by increasing pressure externally to the formable surface and/or reducing pressure in the transparent chamber by an actuation mechanism. Two actuation principles can be used for switching between relaxed and active states:

(1) "Close actuation system" where each Active and Transparent chamber is connected to the Actuator to transfer the corresponding fluid to the active chamber and from transparent chamber for the active state. The corresponding system is used by the Sensor Cell interaction with a diffractive accommodating ocular implants of the present invention.

(2) "Open actuation system" where only transparent chamber is connected to the Actuator to transfer matching fluid from the transparent chamber for switching to the active state. The corresponding system can be used in diffractive accommodating aphakic IOL with internal actuation or diffractive switchable contact lens.

In either system, the matching fluid is pulled out from the transparent chamber through a mean of connecting the transparent chamber with the exterior of the switchable cell. This can be in a form of a channel in the substrate of the switchable cell which connects the transparent chamber within all diffractive grooves of the guiding surface to the exterior of the switchable cell.

The performance of a diffractive switchable lens in ophthalmic application (ocular implant, corneal inlay, contact lens and spectacles that are designed for presbyopia correction) relies on two functions:

(1) Sensing a need by the wearer of the diffractive switchable ophthalmic lens to focus at far or near, and (2) Actuation diffractive switchable ophthalmic lens for the required focus.

Actuation in case of a spectacle lens does not present an issue as it can be accomplished either manually or electrically by using, for instance, a solenoid but sensing for far or near need for automatic actuation the switching between far and near foci is a great challenge not only for the diffractive switchable spectacles of the present invention but for all switchable types of spectacles, electro-optical type as Em Power, for instance, and it is also a subject of the present invention.

Sensing and actuation of diffractive accommodating ocular implant can be accomplished with Sensor cell where external chamber of the Sensor cell is connected to the transparent chamber of the diffractive accommodating implant of the present invention or both external chamber is connected to transparent chamber and internal chamber of the Sensor cell to the active chamber of the switchable cell of the diffractive accommodating implant of the present invention. There is a great challenge of sensing and/or actuation of a diffractive accommodating lens without a help of Sensor cell by using internal sensing and actuation. Sensing for far or near need by a wearer of any switchable IOL switchable contact lens is a great challenge for presbyopia correction, for instance, by electro-optical ELANZA implant. The system structurally equivalent to one used for sensing the need for far or near focus and actuation of the switching to the desired focus utilized by the diffractive switchable lens of the present invention can also be used for sensing function and triggering to the corresponding far or near focus in any switchable type of ocular implant or contact lens and it is also a subject of the present invention.

BRIEF DESCRIPTION OF THE DRAWINGS

The advantages and features of the present invention will be better understood by the following description when considered in conjunction with the accompanying drawings in which:

FIG. 1 shows a simplest form of switchable cell configuration as a circular disc with rectangular cross-section.

FIG. 2 demonstrates a segment of cross-section of preferred embodiment of a switchable cell in the relaxed state. The switchable cell of this embodiment includes two chambers filled with optical fluids, separated by the film with elasticity to change its shape with a difference in pressure between the chambers. This is so called 5-element switchable cell. The film is free-standing or bonded to the diffractive blazed guiding surface of the optical substrate. One chamber (transparent chamber) between the film and guiding surface is filled with an optical fluid of refractive index that matches or very close to the refractive index of the optical substrate. The other chamber (active chamber) at the opposite side of the film from the transparent chamber is filled by a non-matching fluid of the refractive index that is differ from the refractive index of the optical substrate. In a simpler form of 3-element switchable cell, the ambient medium serves the function of a medium in active chamber. The film surface facing the active chamber is formable surface and its shape together with a difference in refractive indices between the substrate and non-matching fluid define a focusing characteristic of the switchable cell in the relaxed state shown.

FIG. 3 demonstrates the same section of the switchable cell cross-section shown on FIG. 2, but the switchable cell is in the active state with the matching fluid is largely removed from the transparent chamber. A pressure in transparent chamber is lower a pressure in the active chamber so most of the area of the formable surface takes the shape of the corresponding groove of the guiding surface, i.e. the formable surface largely conforms to the shape of the guiding surface. The elastic film must maintain continuity and, as a result, it has deviations from the guiding surface in the areas close to the step transitions between the diffractive grooves. This is on called smoothing area. Light passing through the formable surface of the conformed diffractive shape concentrates at the diffractive focus of the guiding surface itself as its diffractive shape was defined as being against the non-matching fluid. For instance, if the guiding surface is shapes to create (−1)-order Kinoform if facing the medium of the active chamber, the switchable cell in the active state also forms (−1)-order Kinoform with most light forming image at the focus of the (−1)-order of diffraction of the guiding surface. Only a fraction of light that passes through the smoothing area of the formable surface is spread out outside the active state focus. The light "spread out" must have a significant area because the formable surface shape within the smoothing area manifests significant curvatures. Therefore, it is most likely that the intensity of the highly spread out light at the image plane of the active state diffractive focus is fairly low and, as a result, its impact on the image quality at the diffractive focus is insignificant.

FIG. 7 demonstrates a side view of aphakic diffractive accommodating lens assembled with the anterior and posterior members illustrated on the FIGS. 5 and 6 and switchable cell of the FIG. 4 placed in between. The anterior and posterior members are separated by the width of the actuation members attached to the switchable cell which are bonded to the lens members.

Figure 6:
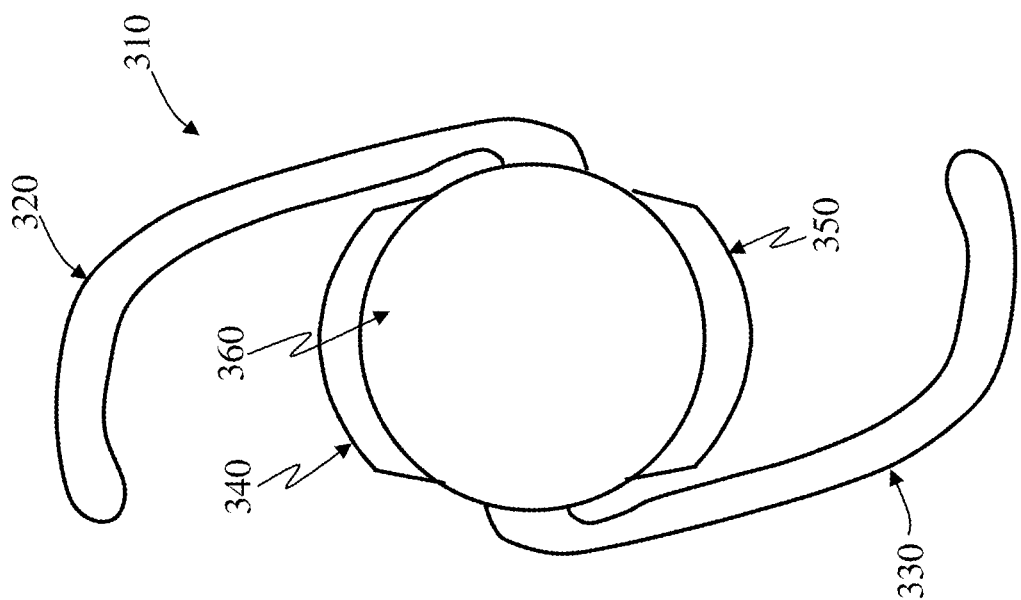
FIG. 6 illustrates front view of the optical posterior member of the diffractive accommodating aphakic IOL with internal actuation. The posterior member is shaped by the posterior optical surface of the diffractive accommodating lens and largely by flat surface anteriorly. In general, the posterior surface of the switchable cell and anterior surface of the posterior member can be curved for a dioptric power contribution. Also, the posterior member may have cut out for placement the switchable cell instead of in the anterior member. The posterior member includes haptics for fixation of the diffractive accommodating lens inside the capsular bag. There are also actuation wings attached to the posterior member optic for bonding to the actuation chambers of the switchable cell shown on the FIG. 4. Again, the structure can be reversed and haptics can be attached to the anterior member and the actuation wings can be placed either on anterior or posterior member.

It is known from clinical observations that due to (a) overall implant diameter that reaches the ciliary body, minimum about 13-13.5 mm, and (b) haptics angulation, a conventional IOL commonly moves along the optical axis with accommodation by about 10-100 microns due to a compression of the lens haptics attached to the lens optical body by circumference of the ciliary body. The ciliary body present circumferentially around the internal surface of the eye globe and incorporates ciliary muscle that changes its shape with accommodation thus altering the ciliary body shape affecting a pressure on the haptic as the supporting member of the implant. The magnitude of movement by conventional IOL is insufficient for a meaningful power change of the eye, besides, a movement can either be forward or backward and, therefore, this movement is commonly ignored.

Nevertheless, the diffractive switchable IOL design demonstrated on FIG. 7, relies on the above clinical observation by using (a) similar overall diameter to respond to a pressure change on an accommodating lens from the ciliary body with eye accommodation and (b) haptics angulation. A compression of the haptics and increase in their angulation with accommodation increases a separation between the anterior and posterior members by tens of microns, i.e. similar magnitude of movement observed with conventional IOL of equivalent lens sizing and haptics angulation. The increase in separation expands the actuation chamber volume because the corresponding actuation member is bonded to anterior and posterior members at its opposite sides. As a result, the matching fluid is pulled out from the transparent chamber of the switchable cell. This in turn, reshapes the formable surface of the switchable cell from the refractive type of the relaxed state for far focus to diffractive type of the active state for near focus. It takes only several hundreds of milliliter of matching fluid transfer to change the switchable cell state and few tens of microns of the separation change is sufficient for the corresponding fluid transfer. With disaccommodation, the haptic takes the original shape reducing the separation into its original relaxed form with the film taking its original shape of formable refractive surface of the minimum strain and the matching fluid is transferred back to the transparent chamber from the actuation chamber.

The structure described in the FIG. 7 serves (a) sensing for a need for far or near focus by the wearer of the implant and (b) actuation for far or near focus. The same structure of the internal actuation described on FIG. 7 can be applied for sensing a need for far and near foci in any type of accommodating optic, for instance, in electro-optical switchable lens such as ELENZA type. In latter case, an actuation member includes electric or magnetic switch instead of optical fluid to trigger electro-optical actuation with the separation increase with ocular accommodation.

FIG. 8 and FIG. 9 demonstrate cross-section views of the switchable cell and actuation members of the diffractive accommodation lens of the FIG. 7 in relaxed state and active state correspondently. The width of the actuation member and as a result, the actuation chamber along the optical axis in the relaxed state (FIG. 8) is shown to be narrower than in active state (FIG. 9) demonstrating the actuation chamber volume increase. The refractive formidable surface of the switchable cell of the FIG. 8 changes into diffraction surface shown on the FIG. 9. Formable surface is the posterior surface of the switchable cell in the FIGS. 8 and 9 and is facing the space between anterior and posterior members. As the diffractive accommodating lens is installed in the eye, the space between anterior and posterior members is filled with aqueous humor and formable surface is facing the aqueous humor of the eye which functions as the active chamber of the switchable cell. This is an example of 3-element switchable cell with "Open actuation system".

FIG. 10 demonstrates front view of the diffractive switchable contact lens. The overall diameter of the lens is likely .gtoreq.14 mm to minimize its movement with eye blinking and gaze change. The contact lens includes balance at the bottom of the lens to maintain the lens meridional orientation. The contact lens also includes actuation ledge at the bottom of the lens to facilitate interaction with lower eyelid when viewing or gaze down for near focus. The actuation ledge connection to the contact lens body is such that it bends with a pressure elevation at the side of the actuation ledge that faces down. The contact lens incorporates switchable cell within its optic zone which is connected to the actuation chamber at the lens periphery.

FIG. 11 and FIG. 12 demonstrate cross-section views of the diffractive switchable contact lens of the FIG. 10 in relaxed state (FIG. 11) and active state (FIG. 12). The switchable cell is located at the lower part of the lens within the optic zone. The guiding surface is facing inside the lens. The base surface of the diffraction guiding surface of the switchable cell in this structure has convex shape to allow the film to be free-standing at the ridges of the guiding surface grooves in the relaxed state. The formable surface faces a narrow anterior chamber towards front of the film which is filled with tear fluid when the lens is fitted on the eye. This chamber functions as active chamber of the switchable cell. The actuation chamber is connected to the transparent chamber for the matching fluid transfer between them. The actuation chamber forming membrane is bonded to the actuation level. The latter turns together with the actuation ledge bend under the pressure from the lower eyelid when the lens wearer looks down for near focus, FIG. 12. The actuation level turn expands the actuation chamber thus reducing inside pressure that, in turn, pulls out the matching fluid from the transparence chamber for the switchable cell transfer from refractive relaxed state for far focus to diffractive active state for near focus.

A simpler structure is also possible with formable surface being a part of the back surface of the contact lens and facing the tear layer over the anterior surface of the eye. In this arrangement the base surface of the guiding surface is concave and the film is likely bonded to the ridges of the guiding surface grooves to maintain film contact with the ridges. Bonding is an addition manufacture step which is a downside of this structure. It is also possible to have a free-standing film and reply on front surface of the eye to maintain the film proximity to the guiding surface.

In general case, an actuation chamber includes an electrical or magnetic switch responding to the chamber expansion to sense a need for far or near focus by the lens wearer and to trigger switching to far or near focus. With the actuation level turning with the actuation ledge bend under the pressure from the lower eyelid when the wearer of a switchable contact lens looks down for near focus, the actuation chamber containing an electrical or magnetic switch expands triggering the switching from far to near focus.

Figure 14:
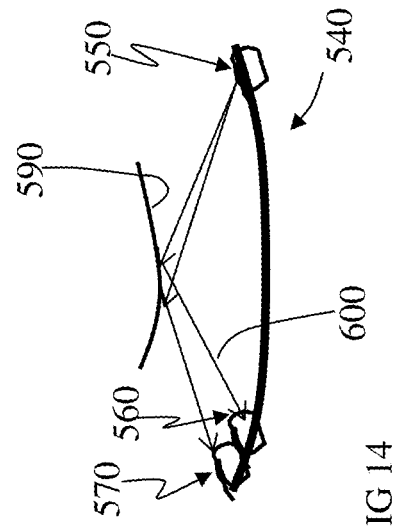
Figure 16:
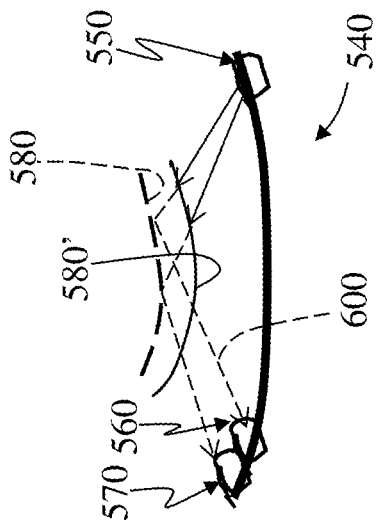
Figure 13:
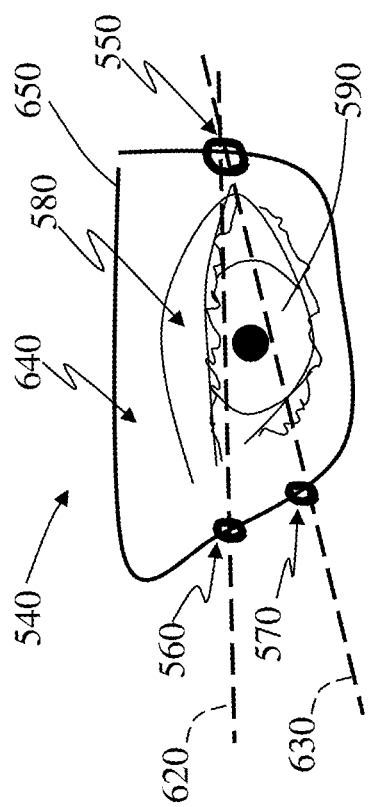
Figure 15:
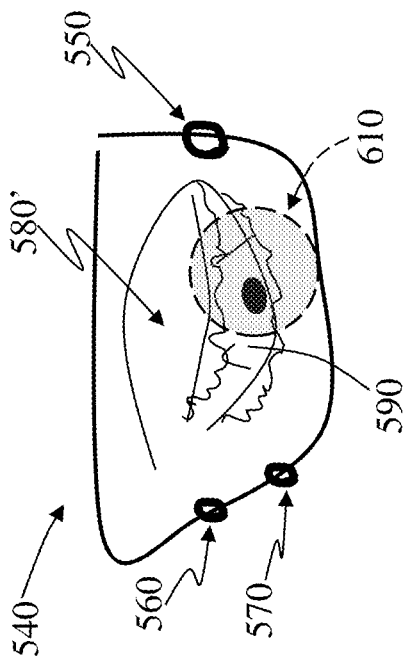

FIG. 13, FIG. 14, FIG. 15 and FIG. 16 depict one half of switchable spectacles that includes switchable spectacle lens to demonstrate sensing a need for far or near focus. The switchable lens may be diffractive switchable lens of the present invention or any type of switchable spectacle lens with the only requirement to utilize the common optical arrangement of bifocal and progressive spectacles for presbyopia correction where the spectacles wearer looks straight forward for far focus and dawn for near focus. The FIG. 13 shows front view of right half of switchable spectacles, i.e. framed right switchable spectacle lens in this case. The IR emitter is installed at one side of the switchable spectacle lens either on the switchable spectacle lens periphery or frame, and an IR sensor is installed on the opposite side of the switchable spectacle lens, also either at the switchable spectacle lens periphery or frame. The IR emitter and IR sensor are installed in approximately horizontal plane that is crossed by the upper eyelid movement between open and closed eye conditions. FIG. 14 is upper view of the spectacles half shown on the FIG. 13: the IR radiation is directed towards front surface (cornea and sclera) of the eye ball by the IR emitter and reaches IR sensor upon reflection off the reflective front surface (cornea and sclera) of the eye ball. FIG. 15 demonstrates front view of the same half of the spectacles with the wearer is looking down for near focus with the upper eyelid in its lower position. The FIG. 16 shows the upper view of the FIG. 15: IR radiation from the IR emitter is fully or partially obstructed by the upper eyelid thus affecting the amount of IR radiation reaching the IR sensor.

Thus, IR radiation received by the IR sensor changes with upper eyelid moving over the front surface of the eye ball by at least ⅓ of total upper eyelid movement from the position of the opened eye for straight forward gaze to the upper eyelid lowest position in closed eye. Change in IR radiation reaching the IR sensor changes the electrical signal generated by it that triggers switching the switchable spectacle lens between far and near foci. A signal threshold for sensing a need for far or near focus for the automatic triggering for far or near focus is individually programmed. In case of a diffractive switchable spectacle lens of the present invention, switchable cell changes between relaxed state for far focus and active state for near focus. The FIG. 15 shows a switchable cell located at the lower part of the switchable spectacle lens similar to a near zone location in conventional bifocal or progressive spectacles.

The structure described by the FIGS. 13-16 serves for sensing a need for far and near foci and can be applied to any switchable spectacles to switch its switchable spectacle lens between far and near foci, for instance, electro-optical switchable lens of EmPower type. In that case, the disclosed sensing system triggers electro-optical switching between far and near foci.

Figure 17:
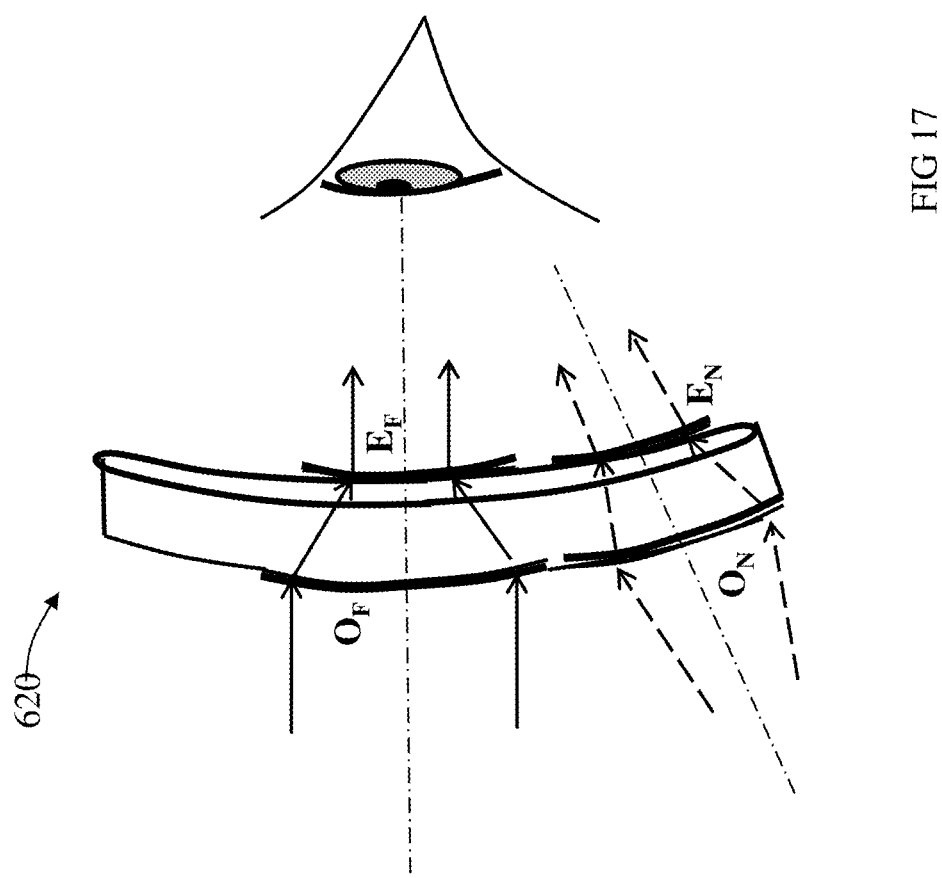

FIG. 17 illustrates a use of switchable cell for low vision application to provide magnification for a visually impaired person. It depicts a spectacle like structure with two pairs of diffractive switchable cells, one pair is for far vision when viewing straight forward and another one is for near vision when looking down. Each pair includes front diffractive switchable cell functioning as objective (high positive power lens) and back diffractive switchable lens functioning as eyepiece (high negative power lens) of the Galilean telescope. They are in relaxed state if a person desires only to observe a general surrounding and a corresponding pair is switched to active states to provide magnification either for far or near vision. The size and lightness of a switchable cell allows to combine them into a pair to form a telescope and even to combine several pairs on a single spectacle like frame for far or near viewing.

DETAILED DESCRIPTION OF THE PREFERRED EMBODIMENTS

FIG. 1 shows a simplest form of switchable cell as a circular disc of D≈3-8 mm diameter and rectangular cross-section of W≈0.05-0.4 mm thickness in ophthalmic applications. The optical axis 100 and segment 110 of the switchable cell are shown. The dimensions of a switchable cell might vary significantly in an engineering optic application.

FIG. 2 demonstrates a segment 110 of the cross-section of a preferred embodiment of a switchable cell in relaxed state. The switchable cell of this embodiment includes transparent chamber 120 filled with matching fluid and active chamber 130 filled with non-matching fluid, separated by the film 140. The active chamber 130 is situated between film 140 and membrane 190. The film 140 is free-standing or bonded to the diffractive blazed guiding surface 150 of the optical substrate 160. Guiding surface 150 is shown as blazed diffraction surface of period L as one of the periods within the segment 110. Diffraction surface periods vary, generally following Eq. 1 with an additional variation to introduce spherical aberration for depth of focus increase in the active state. Film can be made of different elastics, for instance with polydimethylsiloxane also known as PDMS. The PDMS is a Si based organic polymer that has found wide applications in MEMS and microfluidic device fabrication, soft lithography, contact lens manufacturing and device encapsulation. The PDMS material is easily available as SYLGARD 184 Silicone Elastomer Kit from Dow Corning, with mixing in a 1:10 weight ratio. It is inexpensive and fabrication processes for thin film with PDMS include spin-casting, soft lithography (molding).

The optical substrate 160 can be made of any appropriate optical material used in a target application which maintains guiding surface shape with the film compression in the active state, not too soft material. For instance, in IOL application, it can be silicone material (refractive index 1.41 and higher) or hydrophobic acrylic (refractive index 1.46 to 1.56) or even PMMA. Optical fluids of wide range of refractive indices to serve as matching fluid are available. For instance, Laser Liquid from Cargille Laboratories offers optical fluids between 1.293-1.578 refractive indices that are colorless, stable, biocompatible and inert.

The surface facing the active chamber 130 is formable surface 18 which is used to demonstrate optical switching between refractive form of the switchable cell in the relaxed state and diffractive form in the active state.

FIG. 3 demonstrates the same section 110' of the cross-section of the switchable cell, shown in FIG. 2, but in the active state. The film 140' between the transparent chamber 120' and active chamber 130' largely takes the shape of the blazed guiding surface 150 thus reshaping the transparent chamber 120'. The formable surface 180' takes period L at the location of the segment 110' and groove height H of the guiding surface 150 to become blazed diffraction surface of the same periodicity and height as the guiding surface 150. The elastic film 140' must maintain continuity and, as a result, it has a deviation from the guiding surface in the areas 200 close to the step transitions 210 between the diffractive grooves, so called smoothing area. The smoothing area depends on a difference in pressure between the active and transparent chambers and reduces as the difference increases.

The channel 170 is shown to penetrate the deepest portions of the grooves of the guiding surface 150 to allow the matching fluid to escape from the transparent chamber 120' as shown by arrow F, during switchable cell transition to the active state or to fill the transparent chamber during its transition back for the relaxed state. In a simpler form, the channel can be made in a form of a Trench channel, i.e. a channel cut across the cross-sections of the grooves. Optical effect of the Trench channel in active state is likely negligible with narrow enough channel, say 100 microns or less. A trench channel can be made during diffraction guiding grooves fabrication thus lowering cost of the production and desirably but not necessarily, made in a radial orientation to minimize a tearing of the film in transitions between relaxed and active states when the film strain changes. It also desirable to round trench channel edges for the same purpose.

Finite Element Analysis (FEA) was conducted to investigate a conformance of the switchable cell film to the guiding surface with a difference in pressure between the chambers. Technically, Conformance is defined as L'/L where L is a selected period of the guiding surface and L' is the width of the film conforming to the shape the guiding surface at the period L. A non-conformed width S of a given groove L is S=L-L' and is smoothing area or S-dimension.

It has appeared that Conformance is proportional to the guiding surface period L and it reduces with the reduction the period L for the same pressure difference between the active and transparent chambers. Therefore, the FEA was conducted for the smallest period of a selected aperture of the switchable cell.

Example A

A common aperture in ophthalmic application is 5 mm. This is suitable for any ocular implant and contact lens as the pupil at Near focus is commonly within 5 mm diameter. The smallest period $L_{min}$ was calculated as following:

Focal length F=400 mm (2.5 D of Add power); Design wavelength $\lambda_{design}$=0.54 µm. Assuming 1st order diffraction is used for the guiding surface. Guiding surface diffractive groove radii are defined by Eq. 1 and groove height of the same order by the Eq. 2. PDMS substrate was selected to analyze the mechanics of the large groove height H, i.e. at fairly low refractive index n=1.400 (PDMS material) against tear layer or aqueous humor of refractive index n'=1.336. Matching fluid is also has n=1.400 refractive index. This leads to the minimum period $L_{min}$=88 µm and groove height $H_{-1}$=8.4 µm.

A selection of 7 mm aperture would lead to $L_{min}$=62 microns minimum period for the same material and optical parameters selection.

Film thickness of 10 microns was selected to be comparable with the groove height and for its manufacturability. The film can be "free standing" over the guiding surface or "bonded to ridges" of the guiding blazed diffraction surface, for instance, by oxygen plasma process. "Free standing" setup which does not require additional bonding fabrication step was used and a rounding was added to each ridge peak to prevent tearing of the film with the film potentially sliding over the ridges with film strain changes during transitions between active and relaxed states.

A typical Conformance curve shape for different film thicknesses, groove widths and heights can be represented by a curve that rapidly increases with a pressure difference between the chambers initially and then it is slowing down with approachment to a full conformance to the guiding surface. Each groove of a switchable cell has its own Conformance curve with Conformance curve shifts to a lower pressure difference with a groove period increase. Variable film thickness (thicker along a larger period of the guiding surface and thinner along a smaller period) might be beneficial for Conformance consistency for different periods.

General fitting function of a Conformance Curve is:

$$y = \frac{x}{a + b \cdot x + c \cdot x^2 + d \cdot \sqrt{x}} \quad (3)$$

where y=Conformance and x=pressure difference in PSI units.

In case of the example A above for $L_{min}$=88 µm and H=8.4 µm, the parameters of the Conformance Curve are: a=−0.01; b=0.82; c=0.02; d=0.4.

Use of materials with different refractive indices for the optical substrate with the same periodic structure of the guiding surface does not impact diffractive focal length and only impacts the groove height H per the Eq. 2. The periodicity is the most important parameter and the outcome of FEA are valid for different substrate materials. The only effect of the groove height reduction is a force threshold reduction for a transition between relaxed and active states of the switchable cell.

A radial strain of the film in relaxed state can be added to the film to facilitate its return to the original shape in the relaxed state. Film stretching in a direction parallel the base surface of the diffraction guiding surface in case of the film contact with the guiding surface. In case of a radial strain, the Conformance curve shifts to the right, i.e. to higher pressure difference in the horizontal axis. A radial strain of the film can be used to control a force threshold of the transition between relaxed and active states of the switchable cell.

The blazed guiding surface may also include its own "smoothing" at the transitions between the grooves, i.e. instead of having close to the theoretical step transition from one groove to another, the transitions are smoothed out. A guiding surface smoothing would allow (a) to use larger tool radius for the guiding surface manufacturing instead of more expensive and easily damaged single-point diamond tool, and (b) to increase cutting feed-rate of the fabrication of the corresponding surface or mold insert also to reduce the fabrication cost.

The question is on a Diffraction Efficiency (DE) of the switchable cell in active state. The DE geometrical definition was used to calculate DE of the ideal (theoretical) Kinoform with the smoothing defined by S-dimension: Diffraction Efficiency equals the sum of all area of the grooves coinciding with the blazed surface of the theoretical Kinoform to the area of the theoretical Kinoform for selected aperture.

A DE reduces with the increase of fraction of the smoothing area width to the groove period. It has appeared that a linear regression function per smoothing width (S-dimension) defines the Diffraction Efficiency for a given aperture of the switchable cell. For instance, for 5 mm aperture used in the Example A above, the DE is determined by:

$$DE = 100.019 - 0.752 \cdot S \quad (4)$$

where DE=Diffraction Efficiency, and S is smoothing dimension in microns.

For instance, for 5 mm aperture and pressure difference to achieve conformance of about 0.8 at the minimum period $L_{min}$=88 µm, the Diffraction Efficiency of the switchable cell is following:

S≈2H=16.8 µm, say with a rounding of the groove ridges, S=20 µm, i.e. ≈23% of the minimum period of 88 µm is allocated to film "smoothing". Per Eq. 4, the DE=0.85 which is fairly high even in using such conservative assessment of the film conformance.

Figure 4:
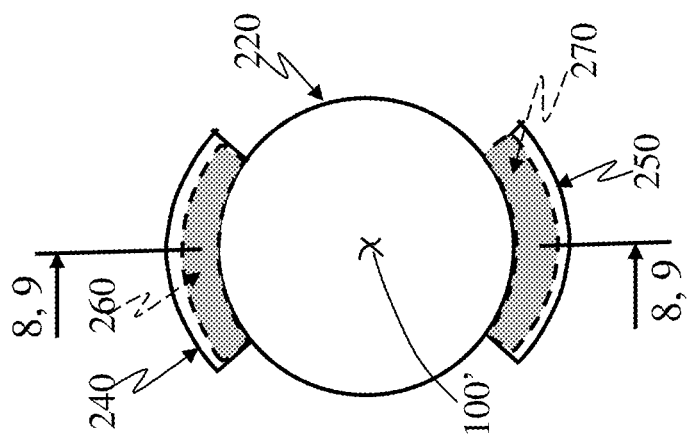
FIG. 4 illustrates front view of switchable cell of diffractive accommodating aphakic IOL with internal actuation. Internal actuation means that the actuation occurs due to an internal interaction between the tens elements. The switchable cell includes at least one but shows two actuation chambers each formed by an elastic membrane with its internal content connected to the transparent chamber of the switchable cell for the matching fluid transfer between the actuation and transparent chambers. The actuation chambers are located at the opposite sides of the switchable cell for balanced actuation. Diffractive accommodating IOL as well as any switchable IOL may also rely on external actuation by the Sensor Cell.

FIG. 4 illustrates front view of switchable cell 220 with optical axis 100' of diffractive accommodating aphakic IOL 230 with internal actuation. The switchable cell 220 is joint with two actuation members 240, 250 that incorporate actuation chambers 260, 270 correspondently. An actuation chamber is formed by an elastic membrane to enable it to change its volume if the actuation member is stretched out.

Figure 5:
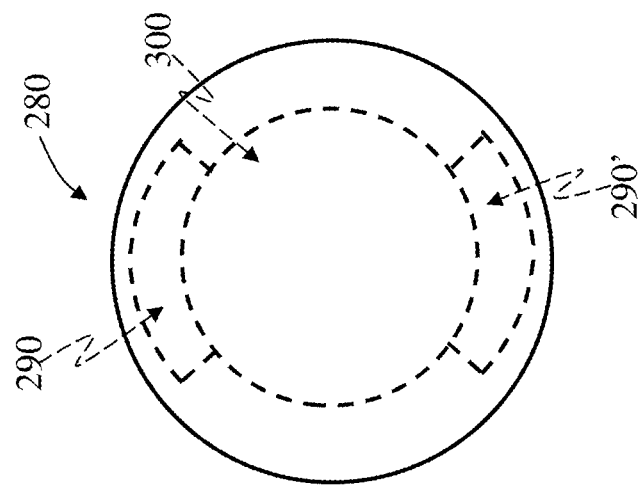
FIG. 5 shows front view of the optical anterior member of the diffractive accommodating aphakic IOL with internal actuation. The anterior member is shaped by the anterior optical surface of the diffractive accommodating lens and largely flat surface posteriorly. The FIG. 5 also shows a cut out on the back of the anterior member for placement of the switchable cell of the FIG. 4.

FIG. 5 shows front view of the anterior member 280 of the diffractive accommodating aphakic IOL 230 with internal actuation. The anterior member 280 is shaped by the anterior optical surface of the diffractive accommodating lens 230 and largely flat surface posteriorly. The FIG. 5 also shows a cut out 300 on the back of the anterior member for placement the switchable cell 220 joined by the cut outs 290, 290' for placement the actuation members 240, 250.

FIG. 6 illustrates front view of the posterior member 310 of the diffractive accommodating aphakic IOL 230 with internal actuation. The posterior member 310 includes haptics 320, 330 attached to the posterior member optic body 360 for fixation the diffractive accommodating aphakic IOL 230 inside the capsular bag of the eye. The posterior member optic body 360 is shaped by the posterior optical surface of the diffractive accommodating lens 230 and largely flat surface anteriorly. There are also actuation wings 340, 350 attached to the posterior member optic body 360 to serve for bonding the posterior member 310 to the corresponding actuation members 240, 250.

FIG. 7 demonstrates side view of aphakic diffractive accommodating lens 230 assembled with the anterior and posterior members 280, 310 and the switchable cell 220. The anterior and posterior members 280, 310 are separated by the width of the actuation members 240, 250. The optic diameter of the anterior member 280 is shown to be larger the diameter of optic body 360 of the posterior member 310 in order for the haptics 320, 330 that are coming out from the optic body 360 to be in contact with the anterior member 280 at its periphery. It is also shown a slight cut out 285 at the periphery of the anterior member 280 where the angulated haptic 320 rests. The identical cut out is located at the opposite side of the anterior member 280 for resting of the other haptic 330. The aphakic diffractive accommodating lens 230 is shown in two states: relaxed state by the position of haptics 320, 330 and active state by the position of haptics 320', 330'. Front surfaces of the actuation members 240, 250 are bonded to the posterior of the anterior member 280 and posterior surfaces of the actuation members 240, 250 are bounded to the actuation wings 340, 350 of the posterior member 310. 5A volume of the actuation chambers 260, 270 expends with the increase in the separation 370 between the anterior members 280 and posterior member 310. The separation 370 increases with the haptics compression and corresponding angulation change from 320, 330 position to 320', 330' position which results in the haptics attached to the optic 360 of the posterior member 310 pushing the anterior member 280 apart from the posterior member 310 by a magnitude $\Delta_f$. This shift is shown by a new position of the anterior member 280'. Separation 370 increase enlarges volumes of the actuation chambers 260, 270 which pulls out the matching fluid from the transparent chamber of the switchable cell 220. This, in turn, switches the formable surface 380 from the refractive state for far focus into formable surface 390 of the diffractive state for near focus.

FIG. 8 and FIG. 9 demonstrate cross-section views of the switchable cell 220 with actuation members 240, 250 in relaxed state and the switchable cell 220' with actuation members 240', 250' in active state. The width of the actuation members 240, 250 along the optical axis 100' in the relaxed state is shown to be narrower the width of the actuation members 240', 250' in active state. This is to demonstrate that the corresponding actuation chambers 260, 270 in relaxed state is enlarged into actuation chambers 260', 270' in the active state. In turn, it transforms the refractive formidable surface 380 of the switchable cell 220 into diffraction surface 390 of the switchable cell 220'. The formable surface is in contact with aqueous humor in the eye.

FIG. 10 demonstrates front view of the diffractive switchable contact lens 400. The contact lens 400 includes balance 410 at the bottom of the lens to maintain the lens meridional orientation. The contact lens 400 also includes the actuation ledge 420 at the bottom of the lens to facilitate interaction with the lower eyelid when viewing down for near focus similar to a performance of an alternating contact lenses. The contact lens 400 includes a switchable cell 440 within the optic zone 460 which joints the actuation chamber 450.

FIG. 11 and FIG. 12 demonstrate cross-section views of the diffractive switchable contact lens 400 in relaxed state 470, and active state 480 correspondently. The switchable cell 440 is located at the lower part of the lens 400 and consists of optical substrate 490 with its back surface forming a part of the back surface or base of the contact lens 400. The optical substrate 490 can be made of the same material as the contact lens 400 or a different material bonded to the lens depending if the transparent chamber impermeability can be maintained. The guiding surface 500 of the substrate 490 is facing inside the lens with the film 510 free-standing on or bonded to the ridges of the convex shape of the guiding surface 500 in the relaxed state. There is a transparent chamber filled with the matching fluid between the film 510 and guiding surface 500. The formable surface of the film 510 is facing a narrow chamber filled with tear medium when the lens 400 is fitting on the eye. This chamber acts as the active chamber of the switchable cell 440. The actuation chamber 450 is connected to the transparent chamber of the switchable cell 440 for the matching fluid transfer between them to switch between relaxed and active states. The actuation chamber 450 is bonded to the actuation level 520 located inside or adjacent to the actuation ledge 420 shown in relaxed state. As the actuation ledge 420 is bent by the lower eyelid pressure when the contact lens wearer looks down for near focus, the actuation level 520 turns. The actuation level turn expands the actuation chamber 450 in the relaxed state into actuation chamber 450' in the active state by pulling out the matching fluid from the transparent chamber of the switchable cell 440. As the result, the film 510' takes the shape of the guiding surface 500 thus modifying the formable surface into a diffraction surface for near focus. The transition between the relaxed and active states corresponds to a shift by $\Delta_c$ distance between unturned actuation level 520 and turned actuation level 520'.

FIG. 13, FIG. 14, FIG. 15 and FIG. 16 depict right half 540 of switchable spectacles to demonstrate a sensing a need for far or near focus. The FIG. 13 shows front view of right half of the spectacles. It consists of frame 650 and switchable spectacle lens 640. The IR emitter 550 is installed at one side of the switchable spectacle lens 640. An IR sensor 560 is installed on the opposite side of the switchable spectacle lens 640, actually two sensors 560, 570 to provide better sensitivity for sensing. Each IR sensor 560 or 570 and IR emitter 550 lie in approximately horizontal planes 620 and 630 correspondently. The depiction of the eye in the FIG. 13 demonstrates the eye's straight forward gaze for far focus through the switchable spectacle lens 640 with the upper eyelid 580 being in its upper position. FIG. 14 is upper view of the spectacles half 540 shown on the FIG. 13: the IR emission from the IR emitter 600 shown by arrows is reflected off the front surface 590 of the eye ball as shown by solid line 600 and reaches the IR sensor 560 on the opposite side of the frame. FIG. 15 demonstrates front view of the same switchable spectacles half 540 in the condition when the wearer looks down for near focus with the upper eyelid 580' in its lower position. The FIG. 16 shows the upper view of the FIG. 15: IR emission from the IR emitter 550 is fully or partially obstructed by the upper eyelid 580' thus changing the amount of IR radiation received by the IR sensor 560 or both sensors 560, 570. The intended reflection from the front surface 590 of the eye ball is shown by the broken line 600'. The outcome of the radiation obstruction is a lower electrical signal from the IR sensor which triggers an actuation of the switchable cell from relaxed state for far focus into active state for near focus; The FIG. 15 showed the switchable cell 610 located at a lower part of the switchable spectacle lens 640.

FIG. 17 illustrates the use of switchable cell for low vision application to provide magnification for a visually impaired person. It depicts a spectacle like structure 620 with two pairs of diffractive switchable cells $O_F+E_F$ for straight forward far vision (subscript F) and $O_N+E_N$ for down near vision (subscript N). A front diffractive switchable cell $O_F$ or $O_N$ serves as the objective of the Galilean telescope and back diffractive switchable cell $E_F$ or $E_N$ serves as the eyepiece of the corresponding Galilean telescope. High order diffraction can be used to reduce focal lengths in both objective and eyepiece of each pair to shorten the Galilean telescope for its placement onto the spectacle like structure 620.

Although there has been hereinabove described a specific refractive-diffractive switchable optical element in accordance with the present invention for the purpose of illustrating the manner in which the invention may be used to advantage, it should be appreciated that the invention in not limited thereto. This is, the present invention may suitably comprise, consist of; or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A pair of spectacles having a frame and defining a horizontal plane that is generally through the temples and bridge of the pair of spectacles, the pair of spectacles comprising:
   at least one switchable lens attached to the pair of spectacles, the at least one switchable lens configured to switch its foci from a first focal length to a second focal length, where the second focal length is different from the first focal length;
   an infrared emitter disposed at one periphery of the at least one switchable lens and/or frame, the infrared emitter configured to emit an infrared radiation;
   an infrared sensor disposed at an opposite periphery of the at least one switchable lens and/or frame, the infrared sensor configured to detect the infrared radiation from the infrared emitter;
   wherein the at least one switchable lens is configured to switch to its first focal length when the infrared sensor detects a first intensity of the infrared radiation and is configured to switch to its second focal length when the infrared sensor detects a second intensity of the infrared radiation;
   wherein the infrared sensor detects the infrared radiation from the infrared emitter after it has reflected off a front surface of an eye ball of a wearer of the pair of spectacles;
   wherein the infrared sensor is configured to detect the second intensity of the infrared radiation emitted by the infrared emitter after being reflected from the front surface of the eye ball when the wearer is looking downward, wherein the at least one switchable lens switches its foci to the second focal length; and
   wherein the second intensity is zero.

2. The pair of spectacles of claim 1, wherein the infrared sensor is configured to detect the first and/or second intensity of the infrared radiation emitted by the infrared emitter after being reflected from the front surface of the eye ball of the wearer, wherein the at least one switchable lens switches its foci to the corresponding first or second focal length.

3. The pair of spectacles of claim 1, wherein the infrared emitter and infrared sensor are disposed on a second horizontal plane parallel to the horizontal plane.

4. The pair of spectacles of claim 3, including a second infrared sensor disposed on a different horizontal plane in comparison to the second horizontal plane and at the same peripheral side where the first infrared sensor is located.

5. The pair of spectacles of claim 1, wherein the at least one switchable lens switches between the first and second focal lengths dependent upon a change in intensity of infrared radiation emitted by the infrared emitter and detected by the infrared sensor.

6. An optical lens assembly to be worn externally by a wearer, the optical lens assembly comprising:
   at least one switchable lens configured to switch its foci from a first focal length to a second focal length, where the second focal length is different from the first focal length;
   an infrared emitter disposed at one periphery of the at least one switchable lens and/or a frame capturing the at least one switchable lens, the infrared emitter configured to emit an infrared radiation;
   an infrared sensor disposed at an opposite periphery of the at least one switchable lens and/or frame, the infrared sensor configured to detect the infrared radiation from the infrared emitter;
   wherein the at least one switchable lens is configured to switch to its first focal length when the infrared sensor detects a first intensity of the infrared radiation and is configured to switch to its second focal length when the infrared sensor detects a different intensity of the infrared radiation;
   wherein the infrared sensor is configured to detect the different intensity of the infrared radiation emitted by the infrared emitter and reflected from a front surface of an eye ball when a wearer is looking downward; and
   wherein the different intensity is zero.

7. The optical lens assembly of claim 6, wherein the infrared sensor detects the infrared radiation from the infrared emitter after it has reflected from the front surface of the eye ball of the wearer of the optical lens assembly.

8. The optical lens assembly of claim 7, wherein the infrared sensor is configured to detect the first and/or different intensity of the infrared radiation emitted by the infrared emitter after it has reflected from the front surface of the eye ball when the wearer is looking forward or downward.

9. The optical lens assembly of claim 6, wherein the infrared emitter and infrared sensor are disposed along a common plane.

10. The optical lens assembly of claim 9, including a second infrared sensor disposed at a different plane in comparison to the common plane, the second infrared sensor disposed at the peripheral side where the first infrared sensor is located.

11. The optical lens assembly of claim 6, wherein the at least one switchable lens switches between the first and second focal lengths dependent upon a change in intensity of the infrared radiation detected by the infrared sensor of the infrared radiation emitted by the infrared emitter.

12. A pair of spectacles having a frame, the pair of spectacles comprising:
   at least one switchable lens attached to the pair of spectacles, the at least one switchable lens configured to switch its foci from a far focal length to a near focal length, where the near focal length is smaller the far focal length;

an infrared emitter disposed at one side periphery of the at least one switchable lens and/or frame, the infrared emitter configured to emit an infrared radiation;

an infrared sensor disposed at an opposite side periphery of the at least one switchable lens and/or frame, the infrared sensor configured to detect the infrared radiation from the infrared emitter;

wherein the at least one switchable lens is configured to switch to its far focal length when the infrared sensor detects the intensity of infrared radiation that has been emitted and reflected off a front surface of a wearer's eye ball when the wearer is looking forward; and wherein the at least one switchable lens is configured to switch to its near focal length when the infrared sensor detects a reduced intensity or zero intensity of infrared radiation when the infrared radiation is partly or fully blocked from reflecting off the front surface of the wearer's eye ball by an upper eyelid of the wearer when the wearer is looking downward.

13. The pair of spectacles of claim 12, wherein the infrared emitter and infrared sensor are disposed along a common plane.

14. The pair of spectacles of claim 13, including a second infrared sensor disposed at a different plane in comparison to the common plane, where the second infrared sensor is disposed at the peripheral side where the first infrared sensor is located.

* * * * *